(12) United States Patent
Go

(10) Patent No.: US 11,839,518 B2
(45) Date of Patent: Dec. 12, 2023

(54) TREATMENT ASSISTANCE EQUIPMENT

(71) Applicant: Moo Saeng Go, Busan (KR)

(72) Inventor: Moo Saeng Go, Busan (KR)

( * ) Notice: Subject to any disclaimer, the term of this patent is extended or adjusted under 35 U.S.C. 154(b) by 0 days.

(21) Appl. No.: 17/799,640

(22) PCT Filed: Aug. 19, 2020

(86) PCT No.: PCT/KR2020/011061
§ 371 (c)(1),
(2) Date: Aug. 12, 2022

(87) PCT Pub. No.: WO2022/039296
PCT Pub. Date: Feb. 24, 2022

(65) Prior Publication Data
US 2023/0070187 A1 Mar. 9, 2023

(51) Int. Cl.
*A61B 90/50* (2016.01)
*A61G 15/12* (2006.01)
*A61G 15/14* (2006.01)
*F16M 11/00* (2006.01)
*F16M 13/00* (2006.01)
*A61B 90/00* (2016.01)

(52) U.S. Cl.
CPC ............ *A61B 90/50* (2016.02); *A61G 15/125* (2013.01); *A61G 15/14* (2013.01); *F16M 11/00* (2013.01); *F16M 13/00* (2013.01); *A61B 2090/064* (2016.02); *A61B 2090/0807* (2016.02); *A61B 2090/508* (2016.02)

(58) Field of Classification Search
CPC .......... A61B 1/00149; A61B 2090/508; A61B 90/50; B25J 1/02
See application file for complete search history.

(56) References Cited

U.S. PATENT DOCUMENTS

| 5,104,103 A | 4/1992 | Auchinleck et al. |
| 6,632,170 B1 * | 10/2003 | Bohanan ................ A61B 90/50 600/102 |
| 8,271,135 B2 | 9/2012 | Shioda et al. |

(Continued)

FOREIGN PATENT DOCUMENTS

| CN | 103687563 A | 3/2014 |
| CN | 103919591 B | 4/2016 |

(Continued)

*Primary Examiner* — Bradley Duckworth
(74) *Attorney, Agent, or Firm* — Seed IP Law Group LLP

(57) ABSTRACT

The present disclosure provides a treatment assistance apparatus, comprising: a base; a first joint of which one side is coupled to the base to relatively move; a first arm of which one end is rotatably coupled to the other side of the first joint; a second joint of which one side is rotatably coupled to the other end of the first arm; an adapter arm of which one end is coupled to a first adapter to relatively move, and the first adapter is rotatably coupled to the other side of the second joint; a first driving part disposed in the first joint and configured to rotate the first arm; a second driving part disposed in the second joint and configured to rotate the adapter arm; a pressure part configured to stop a relative motion of the first adapter; and a controller configured to control the first driving part, the second driving part and the pressure part.

17 Claims, 14 Drawing Sheets

(56) References Cited

U.S. PATENT DOCUMENTS

| | | | | |
|---|---|---|---|---|
| 8,425,403 | B2* | 4/2013 | Jo | A61B 1/00149 |
| | | | | 600/102 |
| 8,870,141 | B2* | 10/2014 | Abri | F16M 11/24 |
| | | | | 403/93 |
| 9,519,341 | B2* | 12/2016 | Hasegawa | A61B 34/76 |
| 2013/0247919 | A1 | 9/2013 | Chauvette et al. | |
| 2016/0151920 | A1* | 6/2016 | Nakata | B25J 17/0275 |
| | | | | 901/29 |
| 2017/0341232 | A1 | 11/2017 | Perplies et al. | |
| 2019/0223976 | A1 | 7/2019 | Krinninger et al. | |
| 2020/0261161 | A1* | 8/2020 | Frielinghaus | A61B 34/20 |
| 2021/0038343 | A1* | 2/2021 | Sauer | F16C 11/0695 |
| 2022/0047352 | A1* | 2/2022 | Cuzner | F16M 11/2014 |

FOREIGN PATENT DOCUMENTS

| | | |
|---|---|---|
| CN | 107072862 A | 8/2017 |
| CN | 209422103 U | 9/2019 |
| JP | 2003325436 A | 11/2003 |
| JP | 2005204999 A | 8/2005 |
| KR | 10-2019-0058590 A | 5/2019 |
| KR | 10-2019-0140787 A | 12/2019 |
| KR | 10-2020-0074151 A | 6/2020 |
| KR | 10-2020-0076172 A | 6/2020 |
| WO | WO 2019117896 A1 | 6/2019 |

\* cited by examiner

TREATMENT ASSISTANCE EQUIPMENT

BACKGROUND

Technical Field

This disclosure relates to a treatment assistance apparatus for assisting a therapeutic action in a patient's treatment process.

Description of the Related Art

In a general dental treatment process, surgical operation or treatment, various medical apparatuses may be used so that a doctor's treatment activity may be performed smoothly and efficiently. For example, medical apparatuses such as an endoscope, a drill, a suction, a mirror may be used.

The use of such medical apparatuses may be used directly by doctors in treatment process, but in some cases, assistant personnel may use the apparatuses or the apparatuses are used by being attached to simple instruments. Meanwhile, when the medical apparatuses are used by an assistant, it is difficult to fix such an apparatus in an accurate position for a long time. When the medical apparatus is used by being attached to an instrument, it may be difficult to position the medical apparatus at a desired position, and it may not be easy to change the position of the medical apparatus. Therefore, research on treatment aids to solve this problem is being actively conducted.

BRIEF SUMMARY

An aspect provides a treatment assistance apparatus that quickly and accurately move a medical apparatus to a desired position in a course of treatment.

There is provided a treatment assistance apparatus that is easy to position and fix a medical apparatus.

There is provided a treatment assistance apparatus that may be used by being attached to another structure.

There is provided a treatment assistance apparatus that may be used universally for patients in various locations by increasing the portability and mobility.

According to an aspect, there is provided a treatment assistance apparatus including a base, a first joint of which one side is coupled to the base to relatively move, a first arm of which one end is rotatably coupled to the other side of the first joint, a second joint of which one side is rotatably coupled to the other end of the first arm, an adapter arm of which one end is coupled to a first adapter to relatively move, and the first adapter is rotatably coupled to the other side of the second joint, a first driving part disposed in the first joint and configured to rotate the first arm, a second driving part disposed in the second joint and configured to rotate the adapter arm, a pressure part configured to constrain or release a relative motion of the first adapter, and a controller configured to control the first driving part, the second driving part and the pressure part.

According to another aspect, there is provided a treatment assistance apparatus further including a third joint disposed between the other end of the first arm and one side of the second joint, and one end of which is rotatably coupled to the other end of the first arm, a second arm of which one end is rotatably coupled to the other side of the third joint and the other side of which is rotatably coupled to one side of the second joint, and a third driving part disposed in the third joint and configured to rotate the second arm, wherein the controller is configured to control the third driving part.

According to another aspect, there is provided a treatment assistance apparatus, wherein a second adapter that moves relative to the adapter arm is disposed at the other end of the adapter arm, and the pressure part is configured to constrain or release a relative motion of the second adapter.

According to another aspect, there is provided a treatment assistance apparatus, wherein the first adapter and the second adapter are coupled to the adapter arm by a ball joint to freely move relative to each other, and the first adapter and the second adapter are fixed in a state at which the pressure part is operated by the controller.

According to another aspect, there is provided a treatment assistance apparatus, wherein the pressure part is configured to press the ball joint by fluid pressure, magnetic force or electromagnetic force to fix the first adapter and the second adapter.

According to another aspect, there is provided a treatment assistance apparatus, wherein the controller is configured to control the other end of the second joint to be positioned at a first position preset with respect to the base by controlling the first driving part, the second driving part and the third driving part.

According to another aspect, there is provided a treatment assistance apparatus, wherein the controller is configured to control the first driving part, the second driving part and the third driving part so that the first arm and the second arm overlap, and the other side of the second joint is positioned at a second position positioned on an opposite side of the first position with respect to the base.

According to another aspect, there is provided a treatment assistance apparatus, further including a sensor configured to detect pressure, wherein the controller controls the first driving part, the second driving part, the third driving part and the pressure part based on a pressure value detected by the sensor.

According to another aspect, there is provided a treatment assistance apparatus, wherein the controller, when the pressure detected by the sensor is less than a preset value, controls the first driving part, the second driving part and the third driving part, so that the other side of the second joint to be positioned at a third position that is preset in order for the other side of the second joint to be farther from the base.

According to another aspect, there is provided a treatment assistance apparatus, wherein the controller is configured to remove the pressure of the pressure part when the pressure detected by the sensor is less than the preset value.

According to another aspect, there is provided a treatment assistance apparatus, wherein the second arm further includes a first position switch configured to move the other side of the second joint to a first position that is preset, a second position switch configured to move the other side of the second joint to a second position that is preset, and a third position switch configured to move the other side of the second joint to a third position that is preset.

According to another aspect, there is provided a treatment assistance apparatus, wherein the third position switch is configured to remove pressure of the pressure part.

According to another aspect, there is provided a treatment assistance apparatus, wherein the second arm further includes first light disposed between one end and the other end of the second arm, toward a first direction, and second light disposed between one end and the other end of the second arm, toward a second direction opposite to the first direction.

According to another aspect, there is provided a treatment assistance apparatus, wherein the controller is configured to control the first light and the second light, and the controller is configured to control the first light to be turned on when the second art is rotated clockwise and the second light to be turned on when the second arm is rotated counterclockwise.

According to another aspect, there is provided a treatment assistance apparatus, wherein at least one of the adapter arm is disposed.

According to another aspect, there is provided a treatment assistance apparatus, wherein the base is a ring shape, a slide rail is formed on an outer circumferential surface, and the first joint is coupled to the slide rail to slide.

According to another aspect, there is provided a treatment assistance apparatus, wherein the base is a ring shape and comprises a first base ring and a second base ring that rotates along an outer circumferential surface of the first base ring, and the first joint is coupled to the second base ring.

According to another aspect, there is provided a treatment assistance apparatus, wherein the base is coupled to a headrest of a medical chair.

According to another aspect, there is provided a treatment assistance apparatus, wherein the first adapter and the second adapter are coupled to the adapter arm by a ball joint, and are constrained by a first elastic body and a second elastic body, and are released as the pressure part operates by the controller.

According to another aspect, there is provided a treatment assistance apparatus, wherein the pressure part is configured to press the first elastic body and the second elastic body by fluid pressure, magnetic force or electromagnetic force to release constraint of the first adapter and the second adapter.

According to various embodiments of the present disclosure, it can be used by attaching it to a treatment apparatus such as an existing medical chair.

In the case of a mobile type with a separate body, the treatment assistance apparatus according to various embodiments of the present disclosure can be used universally in various treatment environments due to increased portability.

The treatment assistance apparatus according to various embodiments of the present disclosure allows a user to easily move a medical apparatus required in the treatment process to a desired position, and allows the medical apparatus to be fixed quickly.

The treatment assistance apparatus according to various embodiments of the present disclosure may store a user's arbitrarily set position, and may move a medical apparatus to the corresponding position with a simple operation.

DETAILED DESCRIPTION

Hereinafter various example embodiments of the present disclosure are described with reference to the enclosed drawings. The example embodiments and terms used therein are not intended to limit the technology described in this document to a specific embodiment, but it should be understood to cover various modifications, equivalents and/or substitutions of the example embodiments. Regarding the description of the drawings, similar numerals reference may be used for similar components, and redundant description thereof will be omitted. The accompanying drawings are only provided for easy understanding of the example embodiments disclosed in the present specification, and the technical ideas disclosed in the present specification are not limited by the accompanying drawings.

Ending words "module" and "part" for components used in the following description are given or mixed in consideration of only the ease of writing the specification, and do not have distinct meanings or roles by themselves. Also, a singular expression may include a plural expression unless the context clearly dictates otherwise.

In this document, expressions such as "A or B" or "at least one of A and/or B" may include all possible combinations of items listed together. Expressions such as "$1^{st}$," "$2^{nd}$," "first" and "second" may modify corresponding components regardless of order or importance. The expressions are used to distinguish one component from anther, but do not limit the components. When it is stated that a (e.g., first) component is "(operatively or communicatively) coupled with/to" or "connected to" another (e.g., second) component, the component may be directly coupled with/to the another component, or may be connected through another (e.g., third) component.

In this document, "configured to (or set to)" may be, depending on a circumstance, used interchangeably with, for example, "suitable for," "having the ability to," "modified to," "made to," "capable of," or "designed to," in hardware or software. In some circumstances, the expression "an apparatus configured to" may mean that the apparatus is "capable of" with another apparatus or parts.

In this document, terms such as "comprise" or "have" are intended to designate that there are features, numbers, steps, operations, components, parts or combinations thereof described in the specification. It should be understood that the terms do not preclude the possibility of existence or addition of one or more other features, numbers, steps, operations, components, parts or combinations thereof.

Figure 1B:
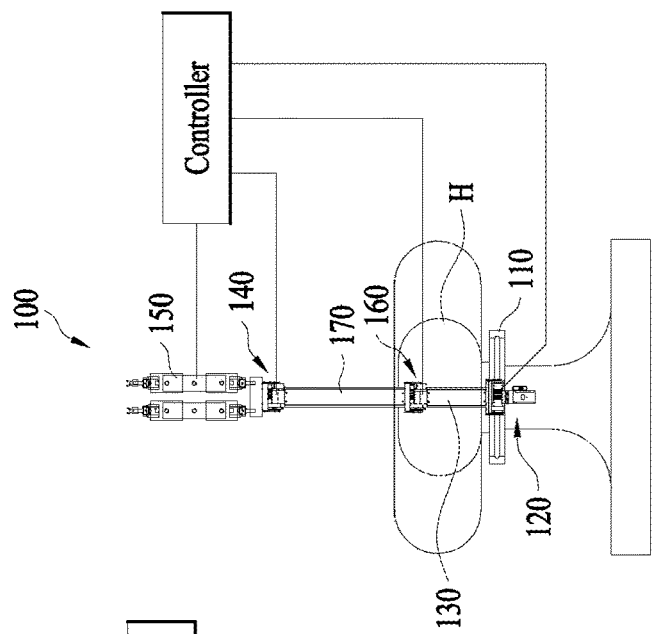
FIG. 1B is a side view of the treatment assistance apparatus.
Figure 1A:
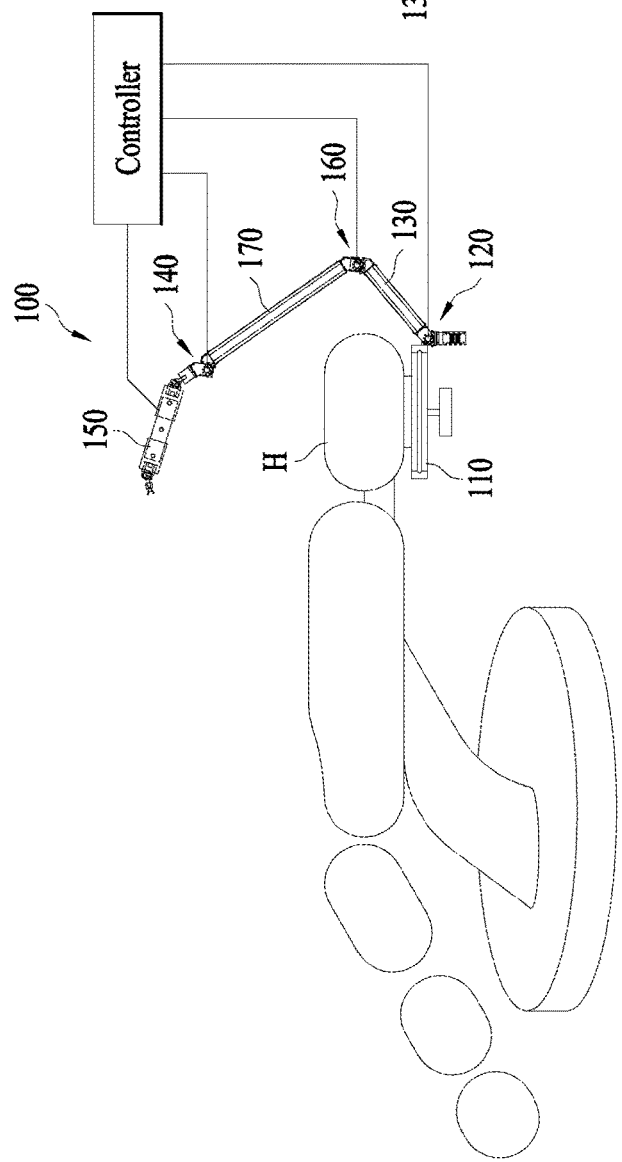
FIG. 1A illustrates a front view in which a treatment assistance apparatus according to an example embodiment of the present disclosure is installed on another medical apparatus.

FIG. 1A illustrates a front view in which a treatment assistance apparatus 100 according to an example embodiment of the present disclosure is installed on another medical apparatus, and FIG. 1B is a side view of the treatment assistance apparatus 100.

The treatment assistance apparatus 100 may include a base 110, a first joint 120, a first arm 130, a third joint 160, a second arm 170, a second joint 140 and an adapter arm 150.

The treatment assistance apparatus 100 of FIGS. 1A and 1B is mounted on a medical chair on which a patient may be seated in a course of a doctor's treatment for utilization, and the treatment assistance apparatus 100 is a type in which the base 110 is mounted on a rear side of a headrest H of the medical chair. In this case, since the treatment assistance apparatus 100 may be additionally mounted on a medical device such as an existing used medical chair, it is economical, and has the advantage that it may be used universally. FIGS. 1A and 1B are illustrated as an example in which the base 110 is mounted on the rear side of the medical chair, but it is not limited thereto, and it may be coupled to a side of the headrest.

FIGS. 1A and 1B illustrate an example where the base 110 is attached to the medical chair for utilization, but it is not limited thereto. For example, the base 110 may be used by being attached to a movable body (not illustrated). With regard to a body, if a moving means such as a wheel is mounted on it for easy movement, and is the body is in a form that provides a stable base to prevent the treatment assistance apparatus 100 of the example embodiment of the present disclosure from falling, the body may be utilized without limitation. For example, a triangular or square-shaped support or a box shape may be utilized. In describing another application example of the treatment assistance apparatus 100, the form in which the base 100 is attached to the body is described. However, the base 110 may be formed integrally with the body, or the base 110 itself may be replaced with the above-described body. As the movement of the treatment assistance apparatus 100 becomes free through the base 110, even if there are several medical chairs, the utilization of the treatment assistance apparatus 100 may be increased by moving and utilizing one treatment assistance apparatus 100.

The treatment assistance apparatus 100 according to an example embodiment may operate as a multi joint robot arm by rotatably connecting the first arm 130, the second arm 170 and the adapter arm 150 to the first joint 120, the second joint 140 and the third joint 160. The treatment assistance apparatus 100 in the form of the multi joint robot arm may be utilized by mounting medical apparatuses 400 and 500 to be described later along with FIGS. 12 and 13 on the adapter arm 150 which is at the end. The treatment assistance apparatus 100 according to the example embodiment may easily and quickly move and fix the medical apparatuses 400 and 500 (see FIGS. 12 and 13) to a position where a user desires. It may position the other side 140b (see FIG. 3) of the second joint 140 at an arbitrary point spaced apart from a patent's head by a predetermined distance in front of the headrest H so that the controller may store the corresponding position, and thereby it is possible to facilitate movement of the treatment assistance apparatus 100. Furthermore, after the user operates and positions the adapter arm 150 that moves relatively freely, the adapter arm 150 may be fixed through a switch operation and so on, so that the medical apparatuses 400 and 500 may be finally positioned at a position desired by the user. More details will be described with the drawings.

Figure 2A:
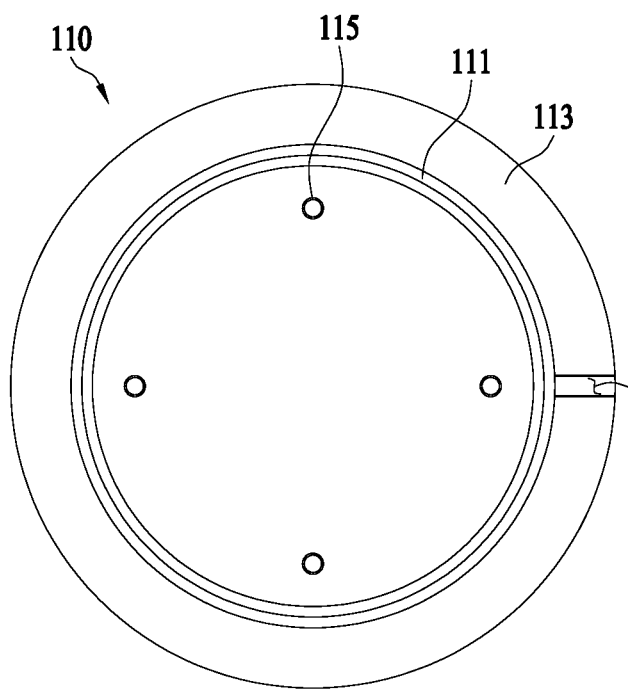
FIG. 2A is a front view of a base according to an example embodiment of the present disclosure.
Figure 2B:
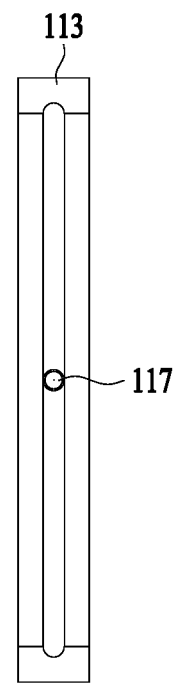
FIG. 2B is a side view of the base.
Figure 2C:
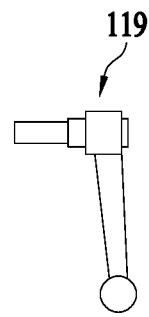
FIG. 2C is a view showing a fixing lever of the base.

FIG. 2A is a front view of the base 110 according to an example embodiment of the present disclosure, FIG. 2B is a side view of the base 110, and FIG. 2C is a view showing a fixing lever 119 of the base 110.

Referring to FIGS. 2A and 2B, the base 110 according to the example embodiment of the present disclosure may include a first base ring 111 and a second base ring 113. The first base ring 111 may serve to be fixed by being coupled to a rear part of the headrest H. The coupling of the first base ring 111 and the headrest H may be performed in various ways. For example, as shown in FIG. 2A, coupling of the first base ring 111 may be coupled to the headrest H through a bolt passing through a fastening hole 115. The second base ring 113 may form a concentric circle with the first base ring 111 and rotate along the outer circumferential surface of the first base ring 111. One side 120a (see FIGS. 3A and 3B) of the first joint 120 according to the example embodiment may be coupled to the second base ring 113. Through this, the first joint 120 may slide and rotate with respect to the first base ring 111. The slide rotation movement of the first base ring 111 and the second base ring 113 may be fixed through the fixing lever 119 illustrated in FIG. 2C. The fixing hole 117 that penetrates in a radial direction is disposed in the second base ring 113, and the fixing lever 119 penetrates the fixing hole 117 to press the outer circumferential surface of the first base ring 111, and thus the slide rotation movement of the first base ring 111 and the second base ring 113 may be stopped and fixed.

FIGS. 2A and 2B illustrate the base 110 formed of the first base ring 111 and the second base ring 113, but other forms are possible. For example, a slide rail (not illustrated) may be formed along the circumferential direction on the outer circumferential surface of the first base ring 111, and one side 120a of the first joint 120 may be coupled to slide along the slide rail.

Figure 3A:
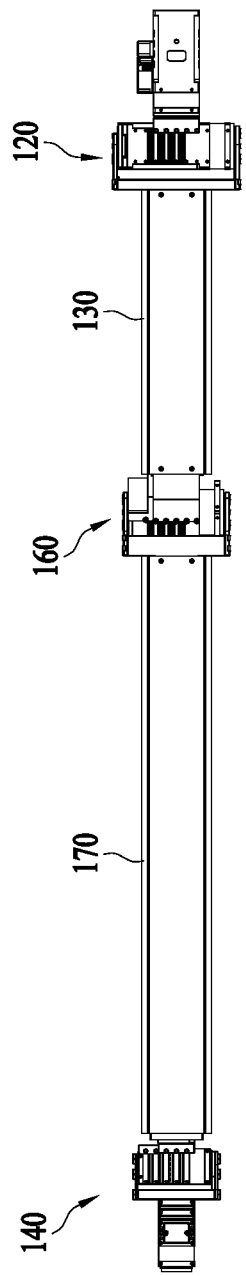
FIG. 3A is a front view of a first arm and a second arm according to an example embodiment of the present disclosure.
Figure 3B:
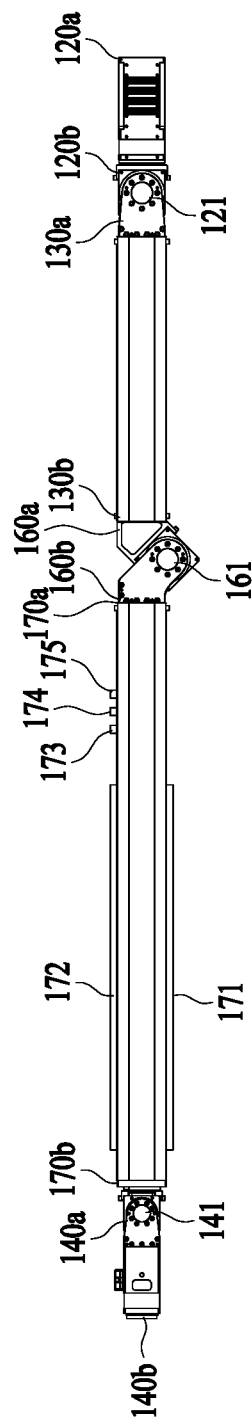
FIG. 3B is a side view of the first arm and the second arm.

FIG. 3A is a front view of the first arm 130 and the second arm 170 according to an example embodiment of the present disclosure, and FIG. 3B is a side view of the first arm 130 and the second arm 170.

Referring to FIGS. 3A and 3B, the first arm 130 and the second arm 170 may be in the form of a rod, and for example, a square pipe may be used. One end 130a of the first arm 130 may be connected to the base 110, and the other end 130b may be connected to the second arm 170. The first arm 130 may allow the second arm 170 to freely move without interfering with the headrest H (see FIGS. 1A and 1B). For example, even if the base 110 is mounted on the headrest H that is larger than the size of the base 110, as the other end 130b of the first arm 130 protrudes from the outside of the headrest H, the first arm 130 may allow the second arm 170 to freely move by bypassing the headrest H. The second arm 170 may be formed to be relatively longer than the first arm 130. The second arm 170 may be positioned so that the other end 170b of the second arm 170 to be positioned in the front space of a patient's face beyond the patient's head that is to be positioned on the headrest H.

The first arm 130 and the second arm 170 according to the example embodiment may be connected to each other by the first joint 120 to the third joint 160 to operate like a multi-joint robot arm.

With regard to the first joint 120 according to the example embodiment, one side 120a may be coupled to the base 110 (see FIGS. 1A and 1B) and the other side 120b may be coupled to one end 130a of the first arm 130. The first joint 120 couples the first arm 130 and the base 110, and may provide at least one rotation shaft so that the first arm 130 is rotatable with respect to the base 110. For example, the first joint 120 may allow the first arm 130 to rotate having one degree of freedom around one rotational axis formed parallel to the tangent direction of the outer circumferential surface. The first joint 120 according to the example embodiment may include a first driving part 121. The first driving part 121 may provide power for rotating the first arm 130 with respect to the base 110. The first driving part 121 may be, for example, a motor.

In description of the first joint 120 according to the example embodiment, the case of rotation with respect to one axis of rotation is described as an example, but it is also possible to increase the degrees of freedom along the three axes that define the three-dimensional space, and in this case, the number of driving parts that provide power may be increased.

With regard to the third joint 160 according to the example embodiment, one side 160a may be coupled to the other end 130b of the first arm 130, and the other end 160b may be coupled to one end 170a of the second arm 170. The third joint 160 couples the first arm 130 and the second arm 170, and may provide at least one rotation shaft so that the second arm 170 is rotatable with respect to the first arm 130. For example, the rotation shaft may be provided in a direction in which the first arm 130 and the second arm 170 may be folded and unfolded like a joint. The third joint 160 according to the example embodiment may include a third driving part 161. The third driving part 161 may provide power for rotating the second arm 170 with respect to the first arm 130. The third driving part 161 may be, for example, a motor.

Figure 4:
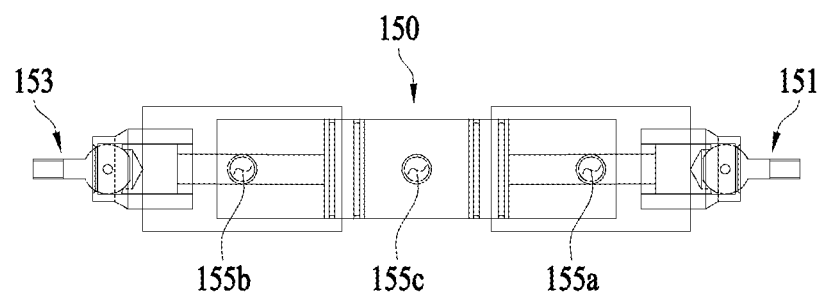
FIG. 4 is a view showing an adapter arm according to an example embodiment of the present disclosure.

With regard to the second joint 140 according to an example embodiment, one side 140a may be coupled to the other end 170b of the second arm 170, and the other side 140b may be coupled to a first adapter 151 (see FIG. 4) of the adapter arm 150 (see FIG. 4). The second joint 140 couples the second arm 170 and the adapter arm 150, and may provide at least one rotation shaft so that the adapter arm 150 is rotatable with respect to the first arm 130. For example, the rotation shaft may be provided in a direction in which the second arm 170 and the adapter arm 150 may be folded and unfolded like a joint. The second joint 140 according to the example embodiment may include a second driving part 141. The second driving part 141 may provide power for rotating the adapter arm 150 with respect to the second arm 170. The second driving part 141 may be, for example, a motor.

First light 171 and second light 172 may be disposed on an outer surface of the first arm 130 or the second arm 170 according the example embodiment. For example, according to the operation of the third joint 160, the first light 171 may be disposed on a side of the second arm 170 among the surfaces where the second arm 170 and the first arm 130 face each other, and the second light 172 may be disposed on the opposite surface. Alternatively, first light (not illustrated) and second light (not illustrated) may be disposed on opposite surfaces of the first arm 130. Alternatively, light may be placed on a corner rather than on a surface. For example, the first light (not illustrated) may be disposed on the second arm 170 among the corners of the sides where the second arm 170 and the first arm 130 face each other, and the second light (not illustrated) may be disposed on the corner of the opposite thereto. Likewise, the first light (not illustrated) and the second light (not illustrated) may be disposed at the corners of opposite surfaces of the first arm 130 side, not the second arm 170 side.

A first position switch 173, a second position switch 174 and a third position switch 175 may be disposed on an outer surface of the first arm 130 or the second arm 170 according to an example embodiment. The first position switch 173 to the third position switch 175 may move the other side 140b of the second joint 140 to a first position (see FIG. 8) to a third position (see FIG. 10) described below. In describing the treatment assistance apparatus 100 according to the example embodiment of the present disclosure, the first position switch 173 to the third position switch 175 have been described in correspondence with the first position to the third position, but this is an example, and the number may be increased or decreased according to the number of positions stored in the controller.

The treatment assistance apparatus 100 according to the example embodiment may include a controller (not illustrated) configured to control the first driving part 121, the second driving part 141, the third driving part 161, the first light 171 and the second light 172. The controller may control whether to operate the first driving part 121 to the third driving part 161, and may control the rotation direction, the rotation speed and a position of the other side 140b of the second joint 140. More specific details will be described later with reference to FIGS. 8 to 10. The controller may control whether the first light 171 and the second light 172 to be turned on according to the operation direction of the third driving part 161. For example, when the second arm 170 and the first arm 130 approach according to an operation of the third driving part 161, the first light 171 may be turned on, and when the first arm 130 and the second arm 170 move away from each other, the second light 172 may be turned on. The driving direction of the second arm 170 may be intuitively figured out through the lighting position of the light.

The controller according to the example embodiment may control a color of the first light 171 and the second light 172 to be changed according to a combination of the first driving part 121 to the third driving part 161 to be driven. For example, it may be controlled that when only the first driving part 121 is driven, a first color (e.g., red) is turned on, when the first driving part 121 and the second driving part 141 move together, a second color (e.g., blue) is turned on, and when the first driving part 121 and the third driving part 161 move together, a third color (e.g., yellow) is turned on.

Figure 5:
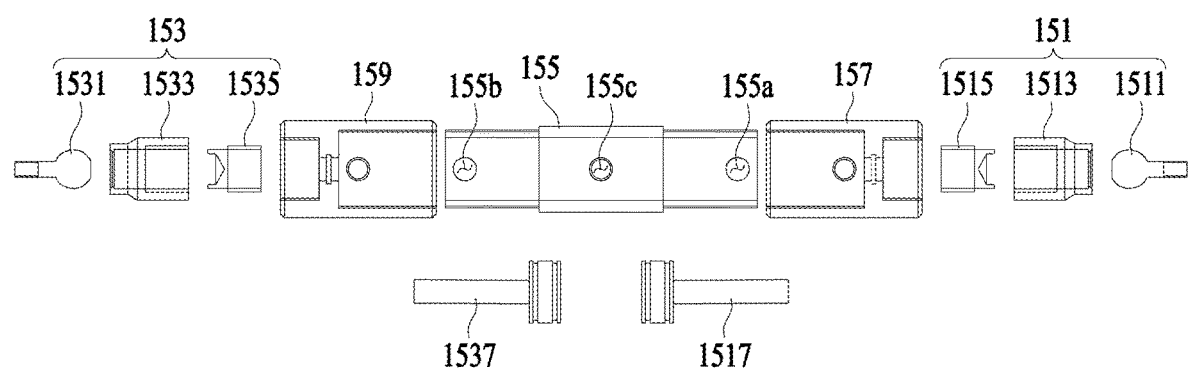
FIG. 5 is an exploded view of an adapter according to an example embodiment of the present disclosure.

FIG. 4 is a view showing the adapter arm 150 according to an example embodiment of the present disclosure, and FIG. 5 is an exploded view of the adapter arm 150 according to an example embodiment of the present disclosure.

The adapter arm 150 of the example embodiment may include the first adapter 151 and a second adapter 153. The first adapter 151 according to the example embodiment may be coupled to the other side 140b of the second joint 140 to couple the second arm 170 and the adapter arm 150. The first adapter 151 is a ball joint type adapter, and may freely and relatively move within a range allowed by the ball joint. Accordingly, the adapter arm 150 may move freely with respect to the second arm 170 within a range allowed by the first adapter 151. For example, pitching, yawing and rolling with respect to the longitudinal axis of the adapter arm 150 are possible. A plurality of adapter arms 150 according to the example embodiment may be disposed.

The second adapter 153 according to the example embodiment may be disposed on the other end of the adapter arm 150 and may be coupled to the medical apparatuses 400 and 500 (see FIGS. 12 and 13) to be mounted on the treatment assistance apparatus 100. For example, the medical apparatuses 400 and 500 of FIGS. 12 and 13 may be coupled. The second adapter 153 also enables pitching, yawing and rolling like the first adapter 151, and accordingly, the medical apparatuses 400 and 500 may freely move with respect to the adapter arm 150 within a range allowed by the second adapter 153.

The first adapter 151 and the second adapter 153 according to the example embodiment may be fixed by a pressure part disposed on the adapter arm 150. The controller may control the pressure part to fix the first adapter 151 and the second adapter 153.

Referring to the detailed structure of the adapter arm 150 with reference to FIG. 5, the adapter arm 150 may include a pushrod guide 155, a first pushrod 1517, a first cap 157, the first adapter 151, a second pushrod 1537, a second cap 159 and the second adapter 153. The pushrod guide 155, the first pushrod 1517, the first cap 157, the second pushrod 1537 and the second cap 159 may be referred to as a pressure part.

The pushrod guide 155 according to the example embodiment provides a basic shape of the adapter arm 150 as a pipe shape, and may include the first pushrod 1517 therein. The pushrod guide 155 may be directly grasped by a user for use, and the first pushrod 1517 may perform a linear motion along the pushrod guide 155. A first hydraulic hole 155a to a third hydraulic hole 155c may be formed in the pushrod guide 155. When fluid flows into the third hydraulic hole 155c located in the center, the first pushrod 1517 and the second pushrod 1537 may be simultaneously pressed. By stopping the flow of the fluid through the third hydraulic hole 155c, the pressure applied to the first pushrod 1517 and the second pushrod 1537 may be removed. Further, the first hydraulic hole 155a and a second hydraulic hole 155b may be disposed to more reliably and quickly remove the pressure applied to the first pushrod 1517 and the second pushrod 1537. For example, when the fluid is introduced intro the first hydraulic hole 155a, the pressure applied to the first pushrod 1517 may be quickly removed, and when the fluid is introduced into the second hydraulic hole 155b, the pressure applied to the second pushrod 1537 may be quickly removed.

The first adapter 151 according to the example embodiment may be disposed at one end of the pushrod guide 155. The first adapter 151 may include a first ball holder 1515, a first ball mount 1513 and a first ball tip 1511. The first ball tip 1511 may have a shape in which a rod-shaped tip protrudes from a spherical body, and a predetermined area may be formed on the opposite surface of the protruding tip to be flat. A tip portion of the first ball tip 1511 may be coupled to the other side 140b of the second joint 140. The first ball mount 1513 may prevent the first ball tip 1511 from being completely separated from the adapter arm 150 and may allow the first ball tip 1511 to move freely. The first ball holder 1515 may receive the force of the first pushrod 1517 to transmit the force to the first ball tip 1511 and fix the first ball tip 1511.

The second adapter 153 according to the example embodiment may be disposed at the other end of the pushrod guide 155. The second adapter 153 may include a second ball holder 1535, a second ball mount 1533 and a second ball tip 1531. The second ball holder 1535 and the second ball mount 1533 may be the same as or similar to the above-described first ball holder 1515 and the first ball mount 1513. A tip portion of the second ball tip 1531 may be coupled to the medical apparatuses 400 and 500.

In the description of the adapter arm 150 according to the example embodiment, the method of fixing the first adapter 151 and the second adapter 153 through hydraulic pressure has been described, but the present disclosure is not limited thereto. For example, it is possible to press a pushrod by using a solenoid using electric force, and it is also possible to press the pushrod by using an on/off magnet or an electromagnet using a permanent magnet and a small amount of power.

Figure 6:
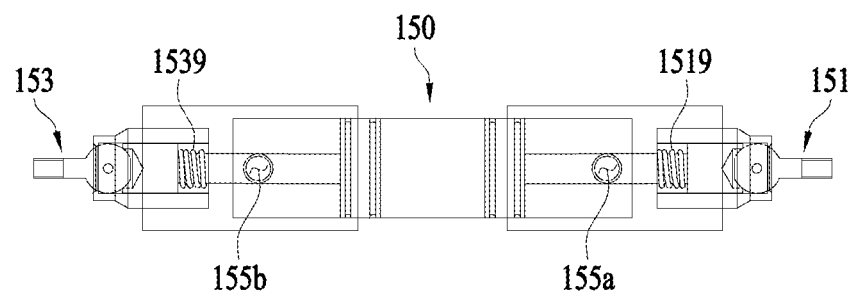
FIG. 6 is a view showing an adapter arm according to another example embodiment of the present disclosure.
Figure 7:
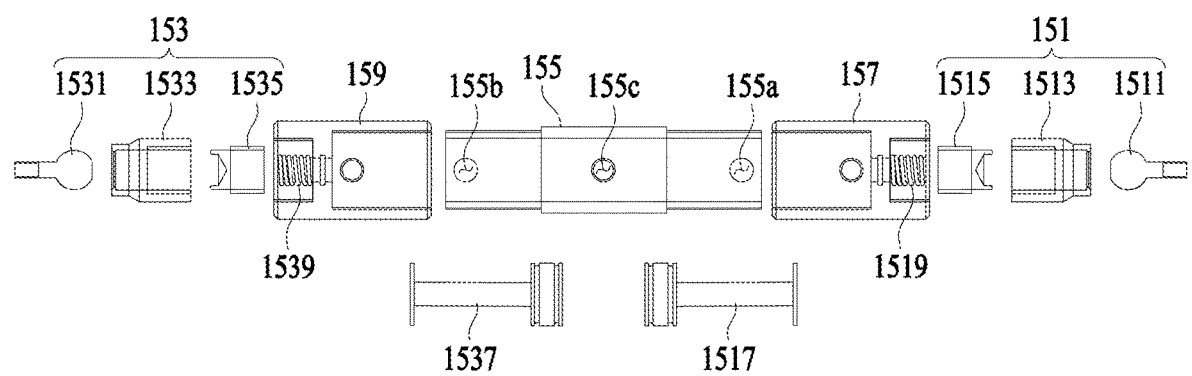
FIG. 7 is an exploded view of an adapter arm according to another example embodiment of the present disclosure.

FIG. 6 is a view showing the adapter arm 150 according to another example embodiment of the present disclosure, and FIG. 7 is an exploded view of the adapter arm 150 according to another example embodiment of the present disclosure.

The adapter arm 150 according to the another embodiment may include the first adapter 151 and the second adapter 153 like the adapter arm 150 of FIGS. 5 and 6. The first adapter 151 and the second adapter 153 are ball joint type adapters, and may freely move relative to each other within a range allowed by a ball joint. For example, pitching, yawing and rolling are possible. The second adapter 153 may be coupled to the medical apparatuses 400 and 500 (see FIGS. 12 and 13) which are to be mounted on the treatment assistant apparatus 100.

Viewing the detailed structure of the adapter arm 150 with reference to FIG. 7, the adapter arm 150 may include the pushrod guide 155, the first pushrod 1517, a first elastic body 1519, the first cap 157, the first adapter 151, the second pushrod 1537, a second elastic body 1539, the second cap 159 and the second adapter 153. The pushrod guide 155, the first pushrod 1517, the first elastic body 1519, the first cap 157, the second pushrod 1537, the second elastic body 1539 and the second cap 159 may be referred to as a pressure part.

The pushrod guide 155 according to the another example embodiment provides a basic shape of the adapter arm 150 as a pipe shape, and may include the first pushrod 1517 therein. The pushrod guide 155 may be directly grasped by a user for use, and the first pushrod 1517 may perform a linear motion along the pushrod guide 155. The first hydraulic hole 155a and the second hydraulic hole 155b may be formed in the pushrod guide 155. Compared with the pushrod guide according to the example embodiment, the difference is that the first elastic body 1519 and the second elastic body 1539 are further included. The first elastic body 1519 may provide elastic force in a direction in which the first pushrod 1517 presses the first ball holder 1515, and the second elastic body 1539 may provide elastic force in a direction in which the second pushrod 1537 presses the second ball holder 1535. In this state, when fluid flows into the first hydraulic hole 155a, the hydraulic pressure overcomes the elastic force of the first elastic body 1519 and pushes the first pushrod 1517 to release the first ball holder 1515, and the movement of the first ball tip 1511 may be free. Likewise, when the fluid flows into the second hydraulic hole 155b, the hydraulic pressure overcomes the elastic force of the second elastic body 1539 and pushes the second pushrod 1537 to release the second ball holder 1535 and the movement of the first ball tip 1531 may be free.

In other words, compared with the adapter arm 150 of FIGS. 4 and 5, there is the difference that the movement of the first tip 1511 and the second ball tip 1531 is normally fixed by the first elastic body 1519 and the second elastic body 1539, and then through the inflow of the fluid, the movement of the first ball tip 1511 and the second ball tip 1531 is free.

Figure 8:
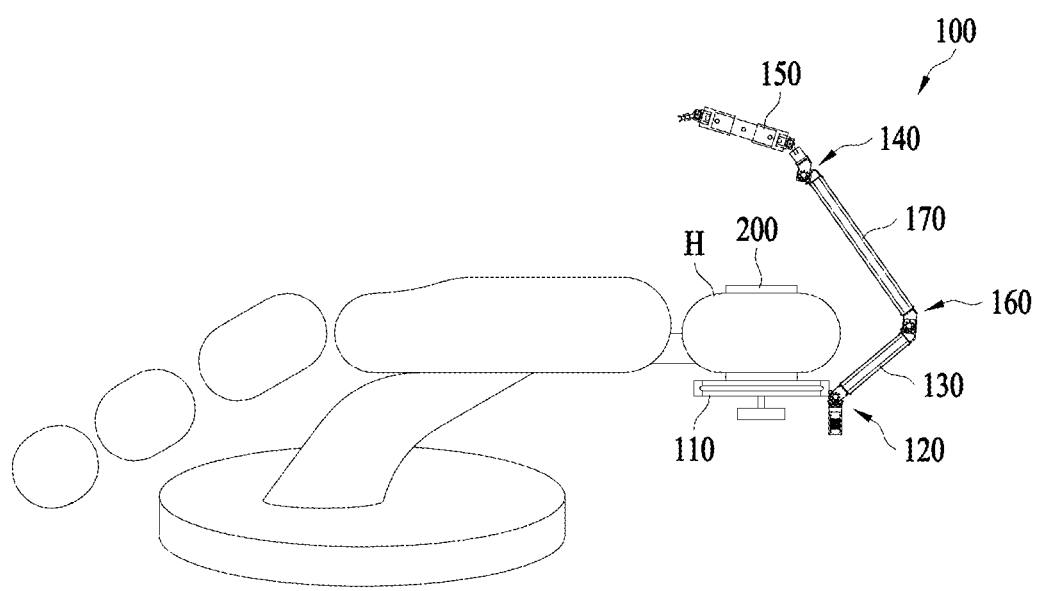
FIG. 8 is a view showing a state in which a treatment assistance apparatus according to an example embodiment of the present disclosure is positioned in a first position.

FIG. 8 is a view showing a state in which the treatment assistance apparatus 100 according to an example embodiment of the present disclosure is positioned in a first position.

The first position according to the example embodiment may refer to an arbitrary place where the other side 140b (see FIGS. 3A and 3B) of the second joint 140 is positioned in front with respect to the headrest H. For example, it may be any point near a patient's face while the patient is seated on a medical chair. The user may adjust the position of the other side 140b of the second joint 140 by operating the first driving part 121 (see FIGS. 3A and 3B) to the third driving part 161 (see FIGS. 3A and 3B), and this position may indicate a point at which the medical apparatuses 400 and 500 may be easily approached to the patient when the adapter arm 150 is operated. The user may store the position of the other side 140b of the second joint 140 at this time, and may move it directly by pressing the first position switch 173.

Figure 9:
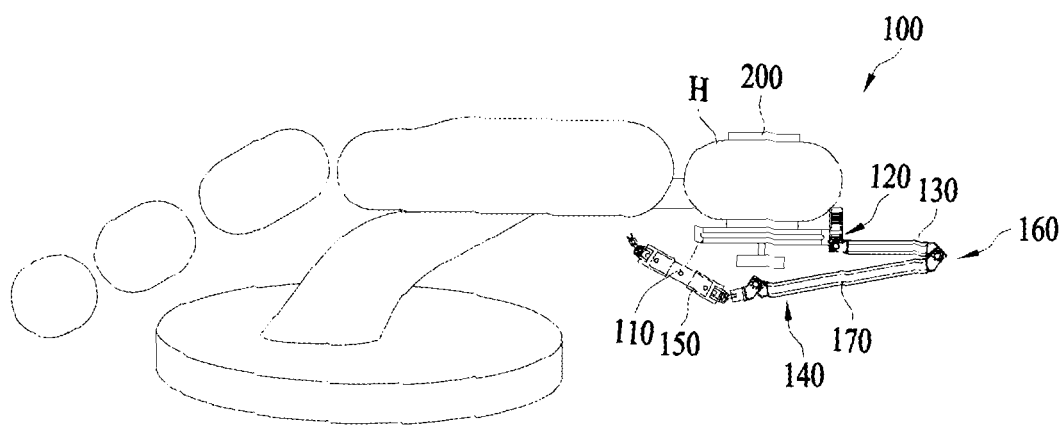
FIG. 9 is a view showing a state in which a treatment assistance apparatus according to an example embodiment of the present disclosure is positioned in a second position.

FIG. 9 is a view showing a state in which the treatment assistance apparatus 100 according to an example embodiment of the present disclosure is positioned in a second position.

The second position according to the example embodiment may refer to an arbitrary place where the other side 140b (see FIGS. 3A and 3B) of the second joint 140 is positioned at the rear with respect to the headrest H. For example, when a medical chair is not used, it may be a position for arranging the treatment assistance apparatus 100 so as not to interfere, such as colliding with nearby objects or colliding with a moving person. The user may adjust the position of the other side 140b of the second joint 140 by operating the first driving part 121 (see FIGS. 3A and 3B) to the third driving part 161 (see FIGS. 3A and 3B), and the position at this time of the other side 140b of the second joint 140 may be stored. It may be directly moved in the second position by the second position switch 174 being pushed.

Figure 10:
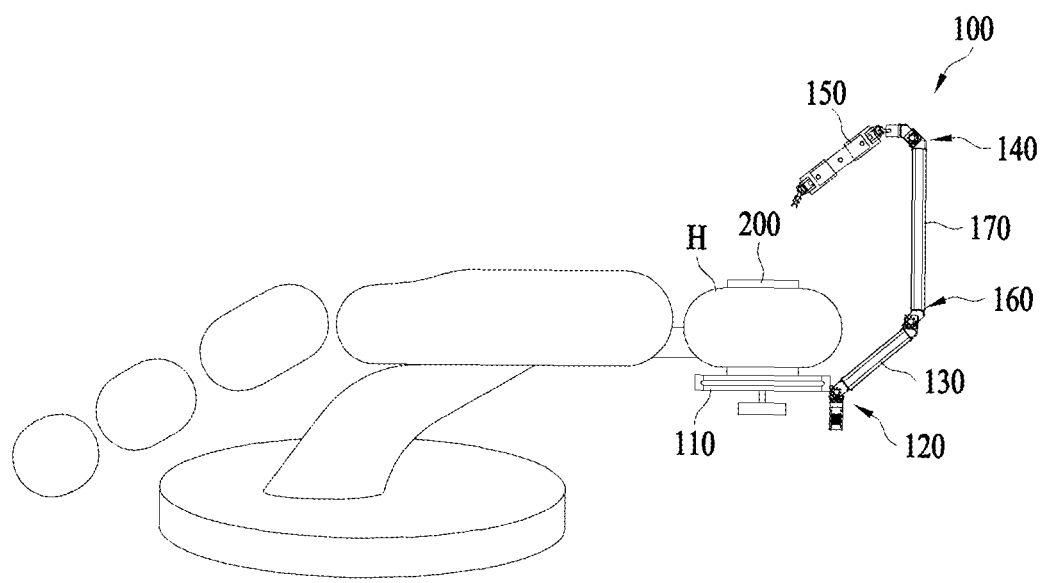
FIG. 10 is a view showing a state in which a treatment assistance apparatus according to an example embodiment of the present disclosure is positioned in a third position.

FIG. 10 is a view showing a state in which the treatment assistance apparatus 100 according to an example embodiment of the present disclosure is positioned in a third position.

The third position according to the example embodiment may refer to an arbitrary position in which the other side 140b (see FIGS. 3A and 3B) of the second joint 140 moves away with respect to the headrest H. For example, when a patient shakes his or her head while a medical apparatus is fixed for treatment, injuries may occur by the medical apparatuses 400 and 500. In preparation for such an unexpected situation, the controller may control the other side 140b of the second joint 140 to be positioned in the third position when a certain condition is detected.

Specifically, the treatment assistance apparatus 100 may include a sensor 200 positioned on the headrest H side. For example, the pressure sensor 200 may be included. While the controller detecting pressure by a patient's head through the pressure sensor 200, when it is determined that the patient shakes his or her head due to a sudden decrease in a pressure value, the controller may control the other side 140b of the second joint 140 to be positioned in the third position and simultaneously release the pressure applied to the first adapter 151 and the second adapter 153, and accordingly it may be possible to prevent injury to the patient.

The third position may be set by a user operating the first driving part 121 to the third driving part 161, and the other side 140b of the second joint 140 may be moved directly by pressing the third position switch 175. In other words, the third position switch 175 may serve as an emergency button.

In describing the treatment assistance apparatus 100 according to an example embodiment of the present disclosure, the cases in which the controller stores three positions as shown in FIGS. 8 to 10 have been described as the example embodiments, but it is not limited thereto, and positions to be stored may be increased or decreased.

Figure 11:
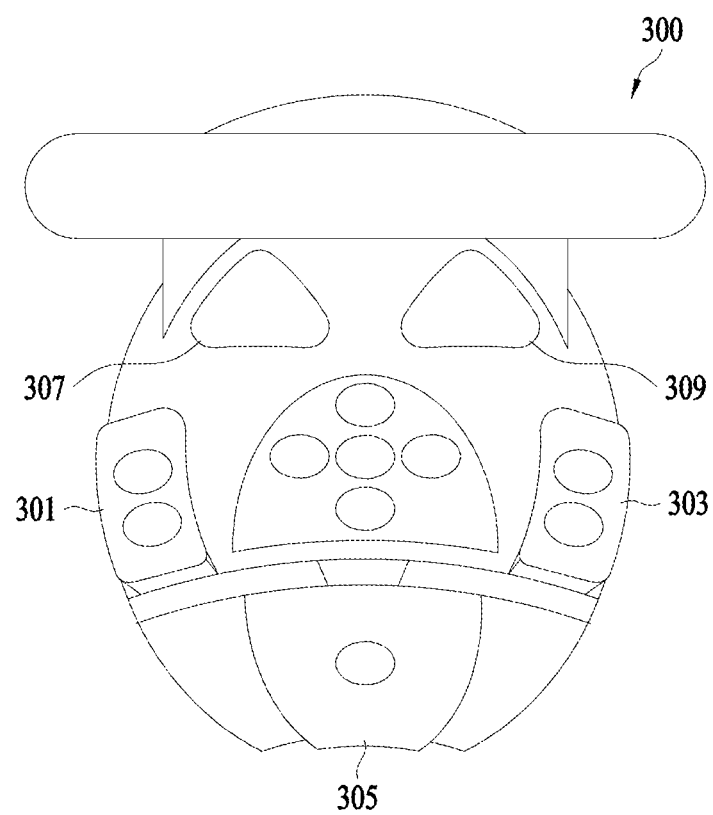
FIG. 11 is a view showing an operation part of a treatment assistance apparatus according to an example embodiment of the present disclosure.

FIG. 11 is a view showing an operation part 300 of the treatment assistance apparatus 100 according to an example embodiment of the present disclosure.

The operation part 300 of the treatment assistance apparatus 100 according to the example embodiment may be in the form of a pedal so that a user may easily operate it with his or her foot. The operation part 300 according to the example embodiment may include a plurality of switches 301, 303, 305, 307 and 309.

For example, a motor to be operated may be selected through a first switch 301, the direction of rotation of the motor may be selected through a second switch 303, and the motor may be driven through a third switch 305. The first adapter 151 may be fixed or released through a fourth switch 307, and the second adapter 153 may be fixed or released through a fifth switch 309. The description regarding the switches is an example, and it may be modified to perform more functions by increasing the number of switches. In addition, the function corresponding to each switch also may be replaced or transformed, in various ways for use.

Figure 12:
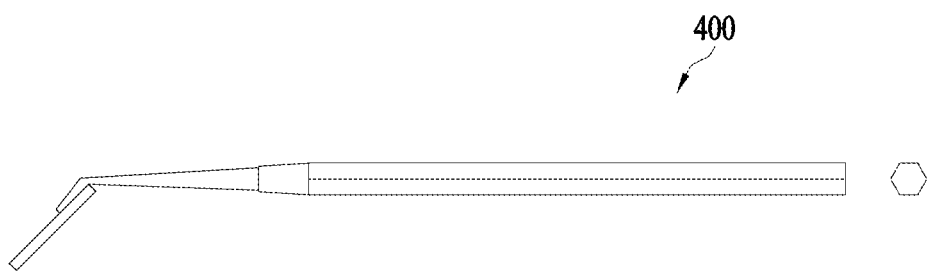
FIG. 12 is a view showing a medical apparatus mounted on a treatment assistance apparatus according to an example embodiment of the present disclosure for utilization.
Figure 13:
FIG. 13 is a view showing another medical apparatus mounted on a treatment assistance apparatus according to an example embodiment of the present disclosure for utilization.

FIGS. 12 and 13 are views showing medical apparatuses 400 and 500 mounted for utilization on the treatment assistance apparatus 100 according to example embodiments of the present disclosure.

For example, a mirror 400 for observing a patient's teeth or a suction tip 500 that may be used in patient's treatment process may be coupled to the second adapter 153 for use. The medical apparatuses 400 and 500 shown in FIGS. 12 and 13 are examples, and in addition to them, various medical apparatuses may be attached and utilized.

Figure 14B:
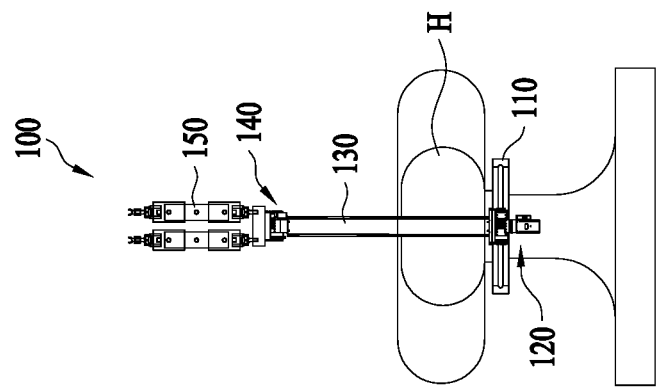
FIG. 14B is a side view of the treatment assistance apparatus.
Figure 14A:
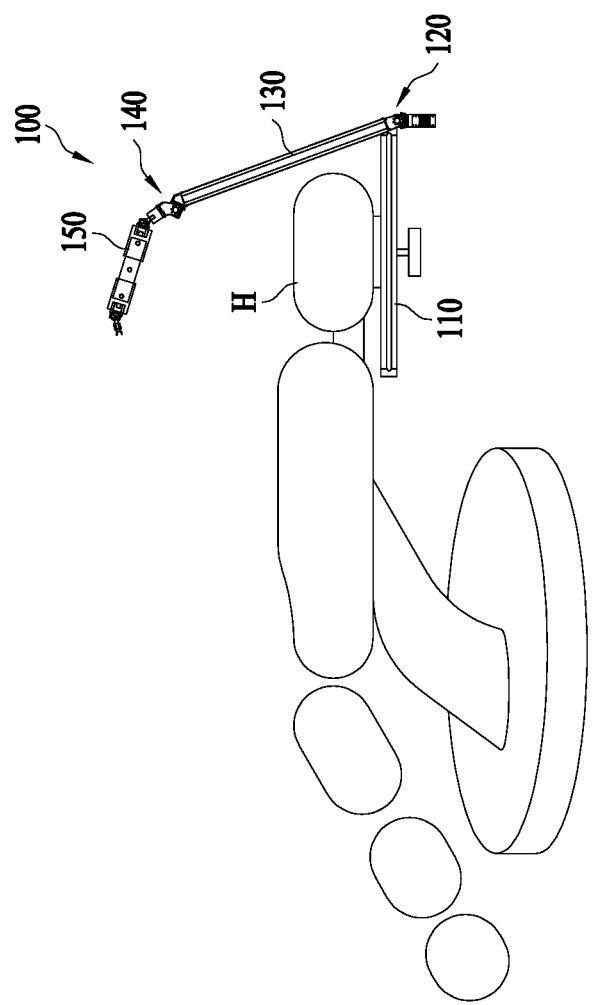
FIG. 14A is a front view of a treatment assistance apparatus according to another example embodiment of the present disclosure being installed on another medical apparatus.

FIG. 14A is a front view of the treatment assistance apparatus 100 according to another example embodiment of the present disclosure being installed on another medical apparatus, and FIG. 14B is a side view of the treatment assistance apparatus 100.

FIGS. 14A and 14B are similar to FIGS. 1A and 1B, but there is a difference in the number of arms constituting the treatment assistance apparatus 100. The treatment assistance apparatus 100 according to another example embodiment may include the base 110, the first joint 120, the first arm 130, the second joint 140 and the adapter arm 150. By making the size of the base 110 to be formed larger than the headrest H compared to the example embodiment of FIGS. 1A and 1B, the number of arms constituting the treatment assistance apparatus 100 may be decreased. Meanwhile, the movable range of a medical apparatus may be narrowed. However, there is an effect of reducing the cost through a simpler structure.

It is apparent to those skilled in the art that the present disclosure may be materialized in other specific forms without departing from the spirit and essential characteristics of the present disclosure.

The above detailed description should not be construed as limiting in all aspects and should be considered as illustrative. The scope of the disclosure should be determined by reasonable interpretation of the appended claims, and all changes within the equivalent scope of the disclosure are included in the scope of the disclosure.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A treatment assistance apparatus, comprising:
a base;
a first joint of which one side is coupled to the base to relatively move;
a first arm of which one end is rotatably coupled to the other side of the first joint;
a second joint of which one side is rotatably coupled to the other end of the first arm;
an adapter arm of which one end is coupled to a first adapter to relatively move, and the first adapter is rotatably coupled to the other side of the second joint;
a first driving part disposed in the first joint and configured to rotate the first arm;
a second driving part disposed in the second joint and configured to rotate the adapter arm;
a pressure part configured to constrain or release a relative motion of the first adapter;
a second configured to detect pressure; and
a controller configured to control the first driving part, the second driving part and the pressure part,
wherein the first adapter is coupled to the adapter arm by a ball joint, and is constrained by a first elastic body, and is released as the pressure part operates by the controller, and
wherein the controller, when the pressure detected by the sensor is less than a preset value, controls the first driving part and the second driving part, so that the other side of the second joint is to be positioned at a third position that is preset in order for the other side of the second joint to be distal from the base.

2. The treatment assistance apparatus of claim 1, further comprising:
a third joint disposed between the other end of the first arm and one side of the second joint, and one end of which is rotatably coupled to the other end of the first arm;
a second arm of which one end is rotatably coupled to the other side of the third joint and the other side of which is rotatably coupled to one side of the second joint; and
a third driving part disposed in the third joint and configured to rotate the second arm, wherein the controller is configured to control the third driving part.

3. The treatment assistance apparatus of claim 2, wherein the controller is configured to control the other side of the second joint to be positioned at a first position preset with respect to the base by controlling the first driving part, the second driving part and the third driving part.

4. The treatment assistance apparatus of claim 3, wherein the controller is configured to control the first driving part, the second driving part and the third driving part so that the first arm and the second arm overlap, and the other side of the second joint is positioned at a second position positioned on an opposite side of the first position with respect to the base.

5. The treatment assistance apparatus of claim 2, wherein the second arm further comprises:
a first position switch configured to move the other side of the second joint to a first position that is preset;
a second position switch configured to move the other side of the second joint to a second position that is preset; and
a third position switch configured to move the other side of the second joint to a third position that is preset.

6. The treatment assistance apparatus of claim 5, wherein the third position switch is configured to remove pressure of the pressure part.

7. The treatment assistance apparatus of claim 2, wherein the second arm further comprises:
a first light disposed between one end and the other end of the second arm, toward a first direction; and
a second light disposed between one end and the other end of the second arm, toward a second direction opposite the first direction.

8. The treatment assistance apparatus of claim 7, wherein the controller is configured to control the first light and the second light, and the controller is configured to control the first light to be turned on when the second arm is rotated clockwise and the second light to be turned on when the second arm is rotated counterclockwise.

9. The treatment assistance apparatus of claim 1, wherein a second adapter that moves relative to the adapter arm is disposed at the other end of the adapter arm, and the pressure part is configured to constrain or release a relative motion of the second adapter.

10. The treatment assistance apparatus of claim 9, wherein the first adapter is coupled to the one end of the adapter arm by a ball joint to freely move relative to each other, and the second adapter is coupled to the other end of the adapter arm by a ball joint to freely move relative to each other, and
the first adapter and the second adapter are fixed in a state at which the pressure part is operated by the controller.

11. The treatment assistance apparatus of claim 10, wherein the pressure part is configured to press the ball joint by fluid pressure, magnetic force or electromagnetic force to fix the first adapter and the second adapter.

12. The treatment assistance apparatus of claim 9, wherein the second adapter is coupled to the other end of the adapter arm by a ball joint, and is constrained by a second elastic body, and is released as the pressure part operates by the controller.

13. The treatment assistance apparatus of claim 12, wherein the pressure part is configured to press the first elastic body and the second elastic body by fluid pressure, magnetic force or electromagnetic force to release constraint of the first adapter and the second adapter.

14. The treatment assistance apparatus of claim 1, wherein the controller is configured to remove the pressure of the pressure part when the pressure detected by the sensor is less than the preset value.

15. The treatment assistance apparatus of claim 1, comprising at least two adapter arms.

16. The treatment assistance apparatus of claim 1, wherein the base is a ring shape and comprises a first base ring and a second base ring that rotates along an outer circumferential surface of the first base ring, and the first joint is coupled to the second base ring.

17. The treatment assistance apparatus of claim 1, wherein the base is coupled to a headrest of a medical chair.

* * * * *